United States Patent [19]

Ishikawa

[11] 4,203,156
[45] May 13, 1980

[54] TITRATION APPARATUS WITH CONTROL MEANS

[75] Inventor: Seiji Ishikawa, Kitakyushu, Japan

[73] Assignee: Mitsubishi Kasei Kogyo Kabushiki Kaisha, Tokyo, Japan

[21] Appl. No.: 973,562

[22] Filed: Dec. 27, 1978

[30] Foreign Application Priority Data

Dec. 27, 1977 [JP] Japan .............................. 52-156397

[51] Int. Cl.² ........................ G01N 27/44; G06G 7/18
[52] U.S. Cl. ................................ 364/500; 204/195 T; 364/497; 364/579
[58] Field of Search ....................... 364/497, 500, 579; 204/195 T, 1 M; 324/29

[56] References Cited

U.S. PATENT DOCUMENTS

| | | | |
|---|---|---|---|
| 3,398,064 | 8/1968 | Propst | 204/1 T |
| 3,649,205 | 3/1972 | Shirakawa et al. | 204/195 T X |
| 3,875,395 | 4/1975 | Jilek | 364/497 |
| 3,879,604 | 4/1975 | Malmvig | 364/497 X |

*Primary Examiner*—G. L. Kaplan
*Attorney, Agent, or Firm*—Oblon, Fisher, Spivak, McClelland & Maier

[57] ABSTRACT

In a titration controlling method and apparatus wherein variations of a titration system caused by intermittent titrations are successively detected electrically, and the quantity of each intermittent titration is controlled by an electric signal obtained by the detection until an end point is reached. According to the present invention, the quantity of each intermittent titration is determined by dividing the quantity of the immediately prior titration, which has been memorized, by the variation of the titration system caused by the immediately prior titration.

4 Claims, 5 Drawing Figures

TITRATION APPARATUS WITH CONTROL MEANS

BACKGROUND OF THE INVENTION

This invention relates to titrating method and apparatus, and more particularly to an improved titration controlling method and apparatus wherein variations in a titration system are successively detected electrically, and the quantity of each intermittent titre is controlled based on an electric signal thus obtained until an end point of the titration is attained.

Recently, automatic titration apparatus are widely used in various fields of chemical analysis. In typical examples of the titration apparatus, variations in the titration system are electrically detected one after another, and the quantity of each intermittent titration is controlled by the electric signal thus obtained until an end point of the titration is determined from the amount of the titre.

In this type of the titration apparatus, however, the end point control becomes inaccurate depending on the titration curve thereof, so that in worst cases the entire titration cannot be performed satisfactorily. More specifically, where the titration is terminated at the end point, as the sensitivity of titration, that is, the variation in the titration system caused by each intermittent titration ordinarily increases abruptly in the vicinity of the equivalent point, so that in order to have an appropriate titration, the quantity of each titration must be reduced in correspondence to the increase in the sensitivity. However, since the increase in the sensitivity widely varies depending on the substance to be titrated, and for this and other reasons such as a delay in the titration reaction and a delay in the detection of the titration result, it is difficult to find out optimum condition for the titrating operation, rendering inaccurate the end point control of the titration which leads to the failure of the entire titration.

Furthermore, according to the conventional process, a precise detection of the equivalent point has been difficult, and, furthermore, owing to the additional requirements of, for instance, recording, preparation of diagrams, and mathematical calculations, the titration operation has been troublesome and complicated.

SUMMARY OF THE INVENTION

A primary object of the present invention is to provide an improved titration method and apparatus wherein the end-point control can be executed at a high efficiency without passing beyond the end point regardless of the type of the titration curve of the titration system, and wherein the equivalent point can be detected easily and precisely.

Another object of the invention is to provide a titration controlling method and apparatus wherein the variation of a titration system caused by each intermittent titration is held substantially constant, and therefore the control of the end point of the titration is facilitated.

Still another object of the invention is to provide a titration controlling method and apparatus wherein the quantity of each intermittent titration is automatically controlled so as to make uniform the sensitivity of the titration, and wherein the entire titration operation can be stopped automatically.

Still another object of the present invention is to provide a titration controlling method and apparatus wherein the results of the titration can be displayed automatically.

A further object of the present invention is to provide a titration controlling method and apparatus wherein any disadvantageous effect caused by the delays in the titration reaction and in the detection of the titration result can be eliminated completely.

According to one aspect of the present invention, there is provided an improved titration controlling method comprising the steps of electrically detecting variations caused in a titration system successively, and controlling the quantity of each intermittent titration by an electric signal obtained at the detection until an end point of the titration is reached, the improvement wherein the quantity of each intermittent titration is determined by a division in which the quantity of the titration immediately prior to the titration, having been memorized, is the dividend, and the variation of the titration system caused by the immediately prior titration is the divisor.

The aforementioned method may further comprise the steps of comparing the quantity of each intermittent titration with the quantity of the immediately prior titration, thereby finding out an inflection point (equivalence point) where the quantity of a titration exceeds the quantity of the immediately prior titration, and utilizing the inflection point as the end point of the titration.

The method may otherwise comprise the steps of comparing successively the signal levels detected in the titration system with preset values, respectively, and determining an instant, where a signal level is equal to the corresponding one of the preset values, as an end point of the titration.

According to another aspect of the present invention, there is provided an improved titration controlling apparatus which comprises an electrolytic cell including a pair of electrolytic electrodes and a detecting electrode, an analog memory temporarily storing an electric signal obtained from the detecting electrode, a subtractor subtracting the thus memorized signal from the electric signal immediately following the first electric signal, a division circuit receiving the output of the subtractor at its dividend terminal, a second analog memory temporarily storing the output of the division circuit, a third analog memory temporarily storing the output of the second analog memory and delivering the output to the divisor terminal of the division circuit, and a voltage/current converter receiving the output of the second analog memory thereby supplying an electrolytic current to the electrolytic electrodes in the electrolytic cell.

According to still another aspect of the present invention there is provided an improved titration controlling apparatus which comprises an electrolytic cell having a pair of electrolytic electrodes and a detecting electrode, a data-processing means, a first voltage/frequency converting means for converting the output from the detecting electrode into a pulse train, a first signal coupling means for optically coupling the output of the first voltage/frequency converting means to an input of the data-processing means, an electrolytic means for intermittently flowing a controlled electrolytic current across the electrolytic electrodes, a second signal coupling means for optically coupling an output of the data-processing means to the input of the electrolytic means, a second voltage/frequency converting means for converting an electrolytic current signal from the electrolytic means into a pulse train, and a third signal coupling means for optically coupling the output of the second voltage/frequency converting means to another input of the data-processing means, the data-processing means further comprising a first operational portion which receives the output from the detecting electrode through the first signal coupling means each time when an intermittent electrolysis is carried out in the electrolytic cell, and calculates and memorizes the variation between the two seccessive outputs from the detecting electrode, a second operational portion wherein the quantity of electricity passed in the immediately prior electrolysis is divided by the variation between the two successive outputs each time when an intermittent electrolysis is carried out in the electrolytic cell, thereby to preset the quantity of electricity for the immediately subsequent electrolysis, a third operational portion which compares the thus preset quantity of electricity with the actual quantity of electricity passed through the electrolytic means, and delivers an electrolysis controlling output when both become coincident thereby to terminate the electrolytic current of each intermittent titration, a fourth operational portion which terminates the entire titration upon finding an inflection point in a variation curve exhibiting variation caused by each intermittent titration, and a fifth operational portion which integrates the quantity of electricity passed through the electrolytic cell and displays the integrated result.

DESCRIPTION OF THE PREFERRED EMBODIMENTS

Figure 1:
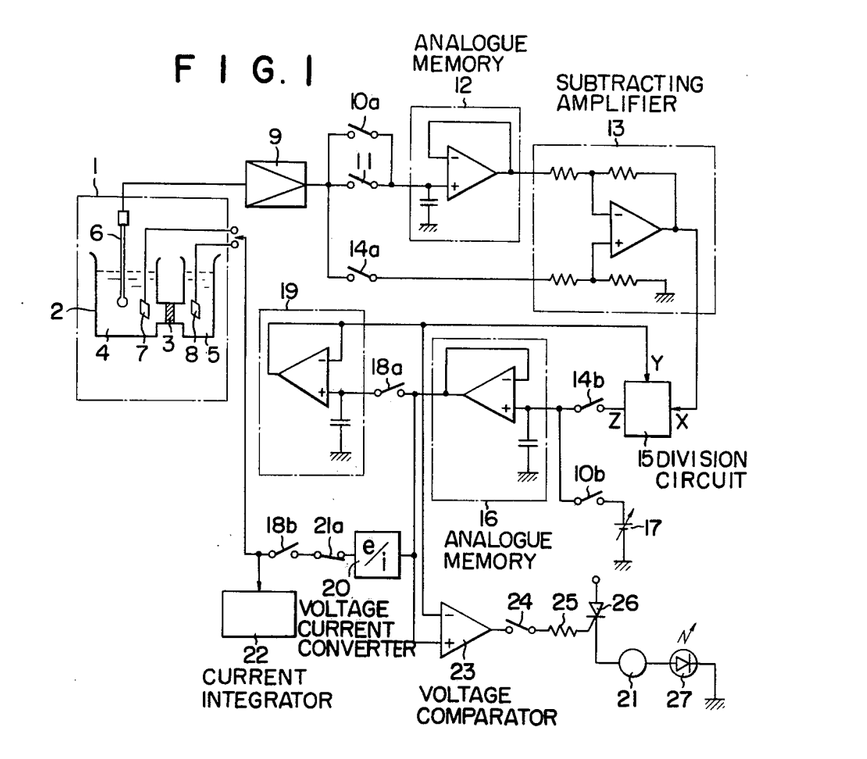
FIG. 1 is a circuit diagram of a titration controlling apparatus utilized to carry out the titration controlling method of the present invention.

Referring first to FIG. 1 showing a circuit diagram of a titration controlling apparatus embodying the present invention, there is provided a cell or a compartment 1 containing a vessel 2. The interior of the vessel 2 is divided into two parts by an electroosmosis membrane 3. The first part of the vessel 2 is filled with a liquid 4 to be titrated, which is a mixture of an electrolyte and an analyte, while the second part of the vessel 2 is filled with a liquid counter-electrode 5. A detecting electrode 6 (for instance a pH electrode, ion electrode, or a platinum electrode) and a generator electrode 7 are immersed in the liquid 4 to be titrated, and a counter electrode 8 is immersed in the liquid counter-electrode 5. The detecting electrode 6 is connected to the input of an amplifier 9 having a high input impedance, and the output of this amplifier 9 is connected through a contact $10_a$ of a first relay and a contact 11 of a second relay which are connected in parallel, to the input of a first analogue memory device 12. The first analogue memory device 12 stores the input signals from the preceding stage for a predetermined interval and delivers these signals successively to an input of a subtracting amplifier 13. The output of the amplifier 9 is also connected to another input of the subtraction amplifier 13 through the contact $14_a$ of a third relay. Thus, the subtraction amplifier 13 operationally amplifies a variation (ΔpH) caused by each titration in the titration system, and the output of the subtraction amplifier 13 is connected to an input of an analogue division circuit 15. The output of the analogue division circuit 15 is connected through another contact $14_b$ of the third relay to one input of a second analogue memory device 16. The other input of the analogue memory device 16 is connected with an initial current setting device 17 (in the form of a simple potentiometer for setting voltage) through the contact $10_b$ of the first relay. The output of the second analogue memory device 16 is connected through the contact $18_a$ of a fourth relay (relay, for effecting electrolysis) to the input of a third analogue memory device 19. The output of the third analogue memory device 19 is connected to the other input of the analogue division circuit 15. Assuming that the input of the divider 15 connected with the output of the subtraction amplifier 13 is designated by X, that the other input of the divider 15 connected with the output of the analogue memory device 19 is designated by Y, and that the output of the divider 15 is designated by Z, the analogue divider 15 performs a division operation of $Z = Y/X$. The output of the second analogue memory device 16 is further connected to the input of a voltage-current converter 20. The output of the converter 20 is connected across the generator electrode 7 and the counter electrode 8, and is also applied to a current integrator 22 through a normally closed contact $21_a$ of a fifth relay and another contact $18_b$ of the fourth relay which are connected in series in a manner to be described hereinafter in more detail. The current integrator 22 may be composed of, for instance, a combination of a V/F converter and a pulse counter having a high accuracy. The output of the second analogue memory device 16 is further connected to one input of a voltage comparator 23, and the output of the third analogue memory device 19 is connected to another input of the voltage comparator 23. The output of the voltage comparator 23 is connected through the contact 24 of a sixth relay and a resistor 25 which are connected in series to the gate electrode of a silicon controlled rectifier 26 (hereinafter abbreviated as SCR), and the SCR 26 is connected in series with the fifth relay 21 and a luminous element 27 displaying the termination of a titrating operation.

The operation of the titration device described above will now be described with reference to a time chart shown in FIG. 2.

Figure 2:
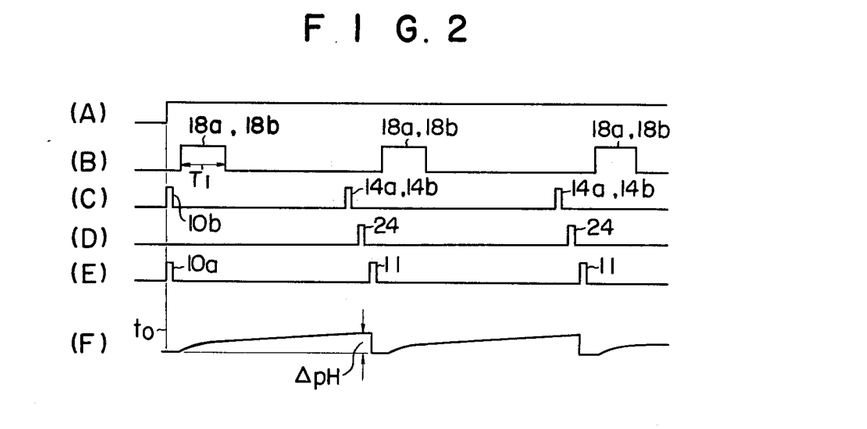
FIG. 2 is a time chart for explaining the operation of the titration controlling apparatus shown in FIG. 1.

Assuming that a titration is started at a time instant $t_o$ shown in FIG. 2(A), relay contacts $10_a$ and $10_b$ are closed as shown in FIGS. 2(C) and 2(E) for short intervals. Thus, a voltage generated by the detecting electrode 6 (in the form of, for instance, a pH electrode) is amplified by the amplifier 9 and then stored in the first analogue memory device 12, and simultaneously a voltage set by the initial electrolytic-current setting device 17 is stored in the second analogue memory device 16.

Then, the fourth relay (not shown), which is an electrolytic operation relay, is energized for a $T_1$ second as shown in FIG. 2(B), and the contact $18_b$ of the same relay is closed, thereby passing an initial current $i_o$ (obtained from the voltage-current converter 20 which converts the output of the analogue memory 16 into a corresponding current) for the $T_1$ second through the generator electrode 7 and the counterelectrode 8. Simultaneously, the output of the second analogue memory device 16 (that is, a voltage $e_{io}$ corresponding to the initial current $i_o$) is, memorized in the third analogue memory device 19 when contact $18_a$ is closed.

It should be noted that the interval $T_1$, in which the fourth relay is operating, represents an electrolytic operation period, and during this period, the first analogue memory device 12 and the subtraction circuit 13 are insulated from the detecting electrode by the contacts $10_a$, 11, and $14_a$ of the first, second, and the third relays, respectively.

After a waiting time subsequent to the termination of the electrolytic period $T_1$ which is necessary to complete the first titrating reaction in the vessel 2, the contacts $14_a$ and $14_b$ of the third relay are closed momentarily as shown in FIG. 2(C) thereby storing a voltage, corresponding to a second titration current immediately following the first titration, in the second analogue memory device 16.

More specifically, upon closure of the contact $14_a$, the output of the amplifier 9, which amplifies the voltage generated by the detecting electrode 6 and has been varied after the previous (or fist) titration, is supplied to one input of the subtraction amplifier 13, while the voltage corresponding to the voltage, which has been obtained from the detecting electrode 6 at the starting time of the titration operation and has been stored in the analogue memory device 12, is supplied to the other input of the subtraction amplifier 13. Accordingly, the subtraction amplifier 13 operationally amplifies the difference between the two input voltages, that is the variation ($\Delta$pH) of the titration system caused by the previous (or first) titration, and delivers its output to the input X of the analogue division circuit 15. To the other input of the analogue division circuit 15 has been applied a voltage (or initial voltage $e_{io}$) corresponding to the previous electrolytic current (or initial electrolytic current $i_o$). Thus, the analogue division circuit 15 performs the following dividing operation:

$$\text{Output} = \frac{\text{voltage }(e_{io})\text{ corresponding to the previous electrolytic current}}{\text{variation }(\Delta\text{pH})\text{ in the titration system caused by the previous titration}} \quad (1)$$

This output is passed through the contact $14_b$ and memorized in the second analogue memory device 16 as a voltage corresponding to the electrolytic current which is to be passed through the electrodes 7 and 8 at the time of the titration immediately following the previous titration.

This voltage corresponding to the above described current (this voltage is hereinafter termed "subsequent titration voltage") memorized in the second analogue memory device 16 and the voltage corresponding to the previous electrolytic current (this voltage is hereinafter termed "previous titration voltage" memorized in the third analogue memory device 19 are compared with each other in the voltage comparator 23. The sense of the output of the voltage comparator 23 is so determined that the output is negative when (previous titration voltage)>(subsequent titration voltage), and is positive when (previous titration voltage)<(subsequent titration voltage). Thus, the contact 24 of the sixth relay is closed momentarily as shown in FIG. 2(D). Thus, when (previous titration voltage)<(subsequent titration voltage), the output of the comparator 23 becomes positive thereby turning the SCR 26 on. The fifth relay 21 and the luminous element 27 displaying the termination of titration are both energized by the conduction of the SCR 26. The titration is actually terminated when the contact 21a of the fifth relay 21 is opened and this condition is displayed by the luminous element 27.

In the case where (previous titration voltage)>(subsequent titration voltage), the output of the comparator 23 becomes negative, and the SCR 26 will not be turned on regardless of the momentary closure of the sixth relay contact 24. Thus, the titration is not terminated, but it proceeds until the contact 11 of the second relay is closed as shown in FIG. 2(E).

Upon closure of the second relay contact 11, the voltage of the detecting electrode 6 which has been varied by the electrolysis of the previous (or initial) titration and amplified by the amplifier 9 is memorized in the analogue memory device 12. The operation thereafter is similar to those described above, and the titration operation is repeated until a relation (previous titration voltage)<(subsequent titration voltage) is obtained at the termination of the titration.

In the operation of the above described titration apparatus each intermittent titration is a constantcurrent (at a varied level) electrolysis of a predetermined period $T_1$, and the electrolytic currents passed in the course of the successive titrations are integrated and displayed automatically by the current integrator 22. The variations of the titration system produced by the successive titrations are indicated in FIG. 2(F).

As will be apparent from the above described operation of the titration apparatus of the present invention, a division operation is carried out in accordance with the equation (1), and the amount of the subsequent electrolytic current (subsequent titre) is determined as a result of the dividing operation. For this reason, the greater is the variation ($\Delta$pH) of the titration system, the smaller will be the result of the dividing operation, which in turn controls the subsequent titre to be smaller, so that the variations of the titration system are controlled ultimately to be brought into a constant value.

Figure 3:
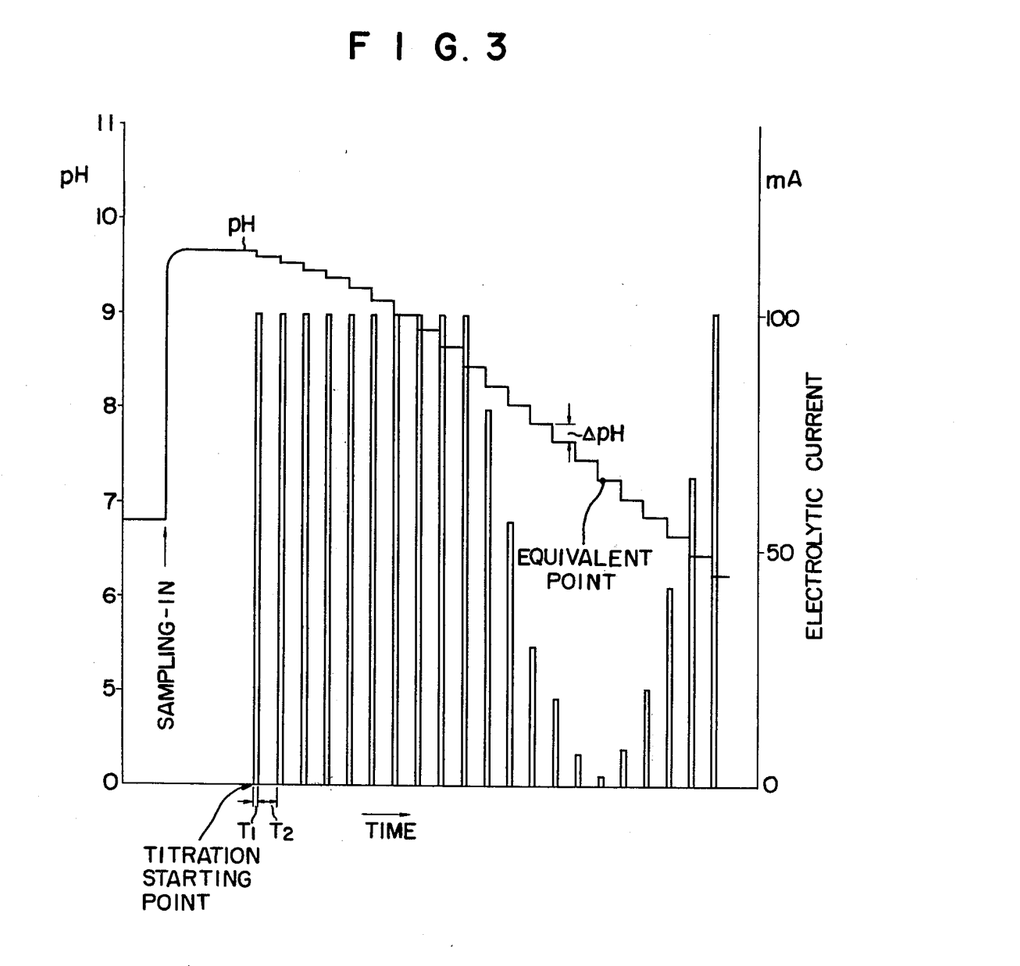
FIG. 3 is graph showing the titration curve and the variation of the titration current in a case where the apparatus is used for the neutralization titration of a base.

FIG. 3 shows one example of a titration curve representing the variation in pH of an alkaline solution caused by intermittent titration current passed therethrough for neutralizing the solution. In plotting this curve, the titration is carried out excessively without detecting the equivalent point for rendering the variation of the titration current to be easily noticeable, and the variation in the titration system caused by the intermittent titration current is exaggerated for facilitating the understanding. It is also apparent from this curve that the variation in pH ($\Delta$pH) of the solution caused by each intermittent titration current is maintained at a constant value near the end point. When the variation of the titration system is maintained smaller, more precise control of end point can be realized. Such an adjustment of the variation of the titration system can be obtained by changing the amplifying factor of the subtraction amplifier 13. In other words, an increase in the amplifying factor reduces the variation caused by each intermittent titration current. However, any reduction in the variation of the titration system elongates the period required for the entire titration, and hence the variation is preferably selected to be in a range of from 0.1 to 0.02 pH.

As is apparent from FIG. 3, in the above described embodiment of the invention, the titrating electrolytic current is minimized at the inflecting point (equivalent point) of the titration curve where the ratio of the variation in the titration system to each intermittent electrolytic current is a maximum. Accordingly, the inflecting point can be easily detected by comparing in the voltage comparator 23 the previous titration voltage corresponding to the previous titration current with the subsequent titration voltage corresponding to the subsequent titration current. That is, before the inflecting point, the titration current is in a reducing trend, and therefore (previous titration voltage)>(subsequent titration voltage). Conversely, a little after the inflecting point, the ratio of the variation in the titration system to the titration current is reduced, and therefore (previous titration voltage)<(subsequent titration voltage). Thus, by the comparison of the two voltages in the comparator 23, the inflecting point can be found at an instant where the result of comparison starts to indicate (previous titration voltage)<(subsequent titration voltage).

It can be noted that, in FIG. 3, the period $T_1$ of each titration and the waiting period $T_2$ corresponding to the time lag in the completion of the reaction and in the detection are both held constant. Ordinarily, $T_1$ is set to be in a range of from 0.5 to 2 seconds, and $T_2$ is set to be in a range of from 5 to 60 seconds.

Although the invention has been described with respect to a preferred embodiment thereof, in the practice of this invention it may be combined with a method of continuous titration effected at a constant velocity. In other words, the titration method according to this invention is extremely effective and of high efficiency in the control near the equivalent point, but it is wasteful in time due to the waiting period between two adjacent intermittent titrations in an initial stage of the titration for a titration system of a high concentration. For obviating this shortcoming, a method is preferred wherein before the equivalent point, a continuous titration (involving no waiting time) is effected at a constant velocity, and when the titration operation comes to the vicinity of the equivalent point, it is transferred to the method of this invention.

For the realization of such a transferring operation, the apparatus may be so arranged that the output of the amplifier 9 having a high input impedance as shown in FIG. 1 is supplied to an arbitrary voltage comparator, not shown, so that the output is compared therein with a preset voltage, and when the output of the amplifier 9 is found to be greater than the preset voltage (far from the end point), the continuous titration is carried out at a constant velocity, and when the output of the amplifier 9 becomes smaller than the preset voltage due to the approach to the end point, the operation is transferred to the intermittent titration of this invention.

Although, in the above described embodiment of the invention, analogue circuits have been used for executing analogue operations, it is apparent that digital operations may also be carried out by replacing the analogue circuits with a microcomputer or the like. In this case, however, it is required that the output of the amplifier 9 is A/D converted, and that the operational results for controlling the electrolytic current and the like are then D/A converted.

Furthermore, although a case where the end point of the titration coincides with the inflection point of the titration curve has been described, it is possible to set the end point of the titration system independently from the inflection point and to terminate the titration at any arbitrary point along the titration curve. This can be realized by supplying a preset voltage, corresponding to the potential of the end point in the titration system, to one input of the voltage comparator 23 in FIG. 1, and the connection of the output of the analogue memory device 12 is changed so that it is connected to the other input of the voltage comparator 23. In this way, while the above described control of the titration is obtained, the fifth relay 21 and the luminous element 27 for displaying the termination of the titration are energized in accordance with the operational timing of the contact 24 when the output of the analogue memory device 12 is equalized to the preset voltage corresponding to the end-point potential.

Furthermore, since the amount of each intermittent titre (quantity of electricity used for the electrolysis) is the product of the amplitude of the electrolytic current and the electrolytic period, the control of the amount of each titre in the present invention can be carried out in a manner different from the above described control of the electrolytic current by controlling the electrolytic period while the electrolytic current is maintained at a constant value, or by controlling both of the electrolytic period and the electrolytic current.

Figure 4:
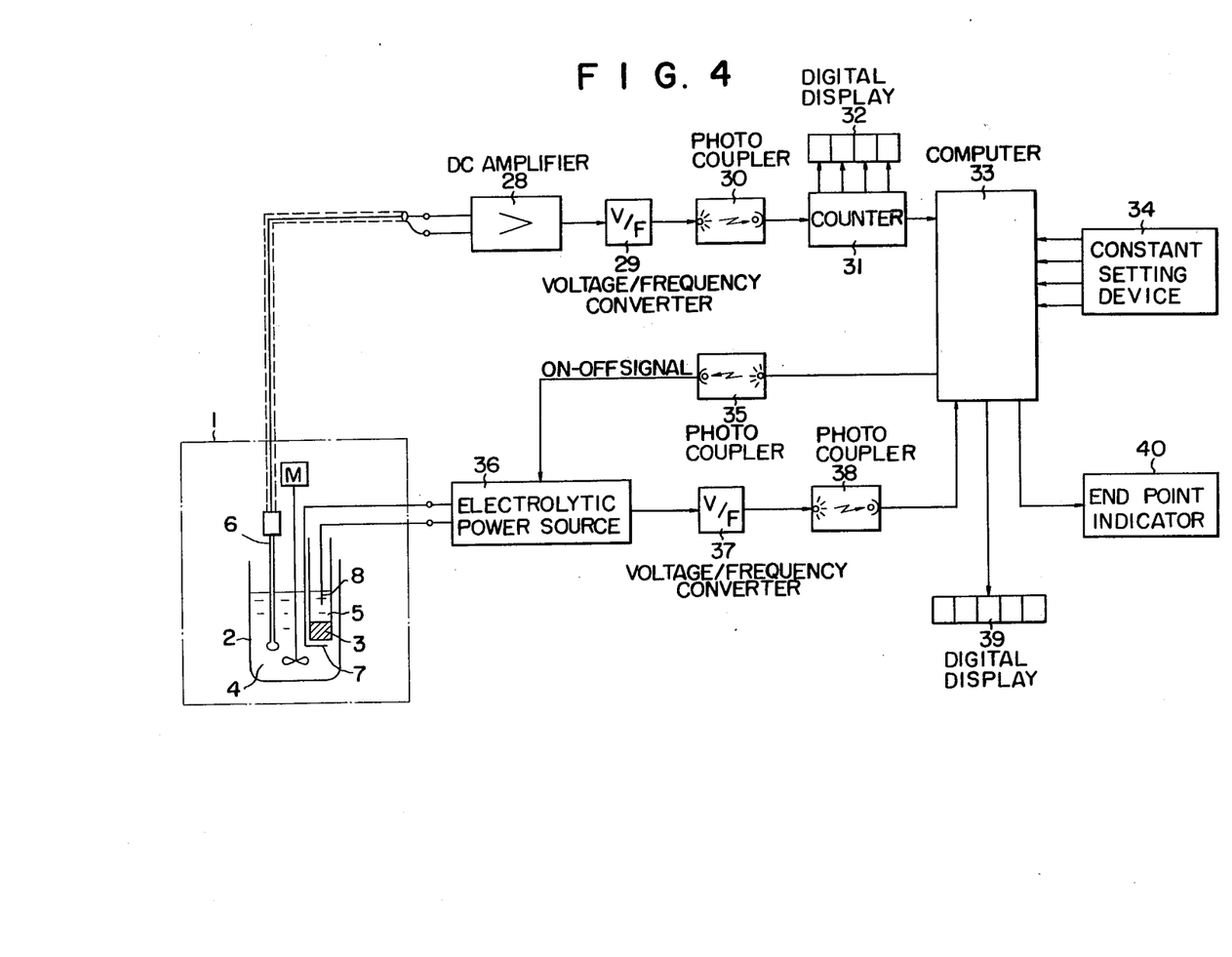
FIG. 4 is a block diagram showing another embodiment of the invention.

In FIG. 4 which is a block diagram showing another embodiment of the present invention, the detecting electrode 6 in the titration vessel 2 provided in the cell 1 (FIG. 1) is connected to the input of a DC amplifier 28 having a high input impedance. The output of the DC amplifier 28 is connected through a voltage-frequency converter 29, a photocoupler 30, and a counter 31 combined with a digital display 32, all connected in series, to an input of a computer 33 including a central processing unit, a subtractor, a divider, a comparator, an end point detector, an integrator, and memory devices which are constructed and operated in the same manner as those shown in FIG. 1. The output of the computer 33 is connected through another photocoupler 35 to an electrolytic power source 36 which supplies electric power across the generator electrode 7 and the counter electrode 8 in the titration vessel 2. A control terminal of the electrolytic power source 36 is connected via a voltage-frequency converter 37 and still another photocoupler 38 to another input of the computer 33. A constant setting device 34 which sets various constants, a digital display device, and an end-point indicator 40 are associated with the computer 33.

The apparatus of this embodiment operates as follows.

An electric signal generated by the detecting electrode 6 is amplified by the DC amplifier 28 having a high input impedance. The output signal of the amplifier 28 is converted by the voltage-frequency converter (hereinafter abbreviated as V-F converter) 29 into a series of pulses which are then supplied to the first photocoupler 30. In the photocoupler 30, the input and the output are mutually coupled optically, and the output thereof is delivered to the counter 31. The counter 31 counts the input pulses for a minute period defined by appropriate gate signals, the count being delivered to the computer 33 while it is displayed by the digital display device 32.

The computer 33 performs a data processing operation as described hereinafter by using both the constants preset in the constant setting device 34 and the data applied from the detecting electrode 6, and it delivers an electrolysis controlling signal based on the results of this operation. The control signal is transmitted through the second photocoupler 35, whose input and output are mutually coupled optically, to the electrolytic power source 36.

The electrolytic power source 36 is operated by the electrolysis control signal so as to pass an electrolytic current between the generator electrode 7 and the counter electrode 8. The power source 36 is further operated to deliver an electric signal proportional to the quantity of electricity used during the electrolysis. This electric signal is V-F converted by the second V-F converter 37 and is sent back through the third photocoupler 38 to the computer 33. The computer 33 then performs the hereinafter described data-processing operation, and the amount of the titration is displayed by the digital display device 39. When the computer 33 detects the end point of the titration, the end-point display device 40 constituted by a plurality of lamps and a buzzer is energized.

A typical titration process utilizing the above described titration apparatus, and the data-processing operation in the computer will now be described.

Firstly a sample is placed in the vessel 2, and the initial output indicative of, for instance $pH_o$, obtained from the detecting electrode 6 and amplified by the DC amplifier 28 is sent through the first V-F converter 29, photocoupler 30, and the counter 31 to the computer 33. In the computer 33, this $pH_o$ is memorized, and a quantity of electricity $Q_1$ preset for the initial electrolysis is read-out from the various constant setting device 34 to be memorized in the computer. Then an electrolysis controlling signal is sent out through the second photocoupler 35 to the electrolytic power source 36. Upon reception of the controlling signal, the power source 36 continuously passes an electric current across the generator electrode 7 and the counter electrode 8, and at the same time, sends back an electric signal indicative of the actual quantity of electricity $q_1$ through the second V-F converter 37 and the third photocoupler 38 to the computer 33.

In the computer 33, while the signal representing the quantity of electricity $q_1$ for the initial electrolysis is counted and memorized, the counted value $q_1$ is compared with the preset quantity of electricity $Q_1$, and when the two values are equal, the electrolysis controlling signal is turned off thereby terminating the initial electrolysis.

After the termination of the initial electrolysis, another output $pH_1$ is sent from the detecting electrode 6 to the computer 33 in the same manner as described above. In the computer 33, this $pH_1$ is compared with the previous value $pH_o$ memorized in the computer, and taking the difference $\Delta pH$ as a divisor and $Q_1$ as a dividend, a division is carried out as follows.

$$Q_2 = K \cdot Q_1 / pH_o - pH_1$$

wherein K is a titration factor preset in the constant setting device 34, and $Q_2$ is the quantity of electricity for the second electrolysis in the titration, which is memorized instead of $Q_1$ in the computer. The electrolysis controlling signal is again generated, thereby enabling the electrolytic power source 36 to carry-out the second electrolysis. The electric signal representing the quantity of electricity $q_2$ used in the course of the second electrolysis is then continuously sent out from the power source 36 to the computer 33 through the second V-F converter 37 and the third photocoupler 38. In the computer 33, the quantity of electricity $Q_2$ for the second electrolysis is compared with the actual value of the quantity of electricity $q_2$ used in the second electrolysis, and when both quantities become equal, the electrolysis controlling signal is terminated. After the termination of the second electrolysis of the titration, still another output $pH_2$ is received by the computer 33, and the operation similar to that described above is repeated until the end point of the titration is reached.

The detection of the end point is carried out in the computer 33 by memorizing these quantities $Q_n$, and comparing the $Q_n$ with $Q_{n-1}$ until a relation $Q_n \geq Q_{n-1}$ is established. That is, the above described operation is carried out while $Q_n < Q_{n-1}$, and when a relation $Q_n \geq Q_{n-1}$ is established, the titration is terminated. This means that the inflection point of the titration curve corresponds to the end point. The result of the titration is indicated in the digital display device 39 which indicates the total sum of the actual quantity of electricity $$\sum_{1}^{E} q_n$$

counted from the initial electrolysis to the final electrolysis.

In the above described embodiment of the present invention, since photocouplers 30, 35, and 38 are used, the detecting circuit, the computer circuit, and the electrolytic circuit are completely insulated electrically from each other by the construction of the photocouplers each comprising, for example, a luminous diode and a phototransistor or a photodiode, and by programming all of the process steps in the computer, the titration can be carried out automatically.

Furthermore, since the electrolysis is controlled in such a manner that the quantity of electricity $Q_n$ calculated as described above is compared in the computer with the actual electrolytic quantity of electricity $q_n$, and the titration control is carried out based on the result of the comparison, a correct control of the titration is always assured regardless of any fluctuation in the electrolytic current supplied from the electrolytic power source.

Although, in the above described embodiment, a case where the invention is applied to coulometry has been described, it is apparent that the invention is also applicable to the ordinary liquid titration method. In the latter case, an electromotive liquid injecting device is controlled instead of the above described quantity of each intermittent titre, thereby adjusting the quantity of each liquid titre.

Figure 5:
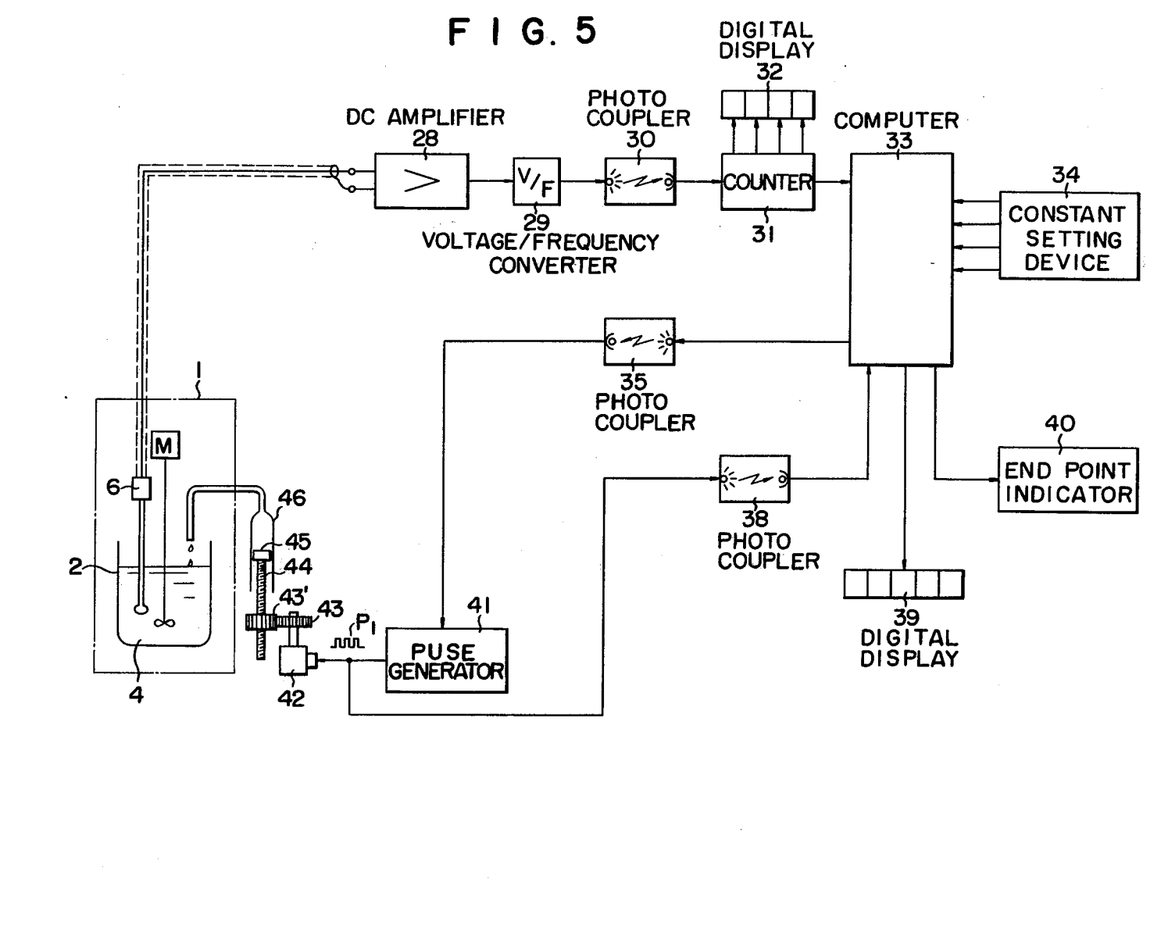
FIG. 5 is a block diagram showing a case where the apparatus of FIG. 4 is applied for a liquid titration.

In FIG. 5, there is illustrated a block diagram of another embodiment of the present invention which is similar to the titration controlling apparatus of FIG. 4, except the construction of the electrolytic cell and the associated devices, and the manner of the titration.

In the cell 1 is provided a titration vessel 2. Within the titration vessel 2 is placed a liquid analyte 4. A titration cylinder 46 is filled with a liquid titrant. In accordance with the upward movement of a screw-threaded bar 44, a piston 45 is pushed upward, and the liquid titrant is dropped into the titration vessel 2. A detecting electrode 6, DC amplifier 28, first voltage/frequency converter 29, first photocoupler 30, counter 31, and computer 33 are all similar to those shown in FIG. 4. The data processing operation of the computer 33 is also similar to that described in connection with the previous embodiment shown in FIG. 4. The electrolysis controlling signal is delivered from the computer 33 through a second photocoupler 35 to a pulse generator 41 that delivers pulses at a constant frequency. The output $P_1$ of the pulse generator 41 is applied to drive a pulse motor 42, and at the same time returned through a third photocoupler 38 to the computer 33. A gear 43 is secured to the rotating shaft of the pulse motor 42. The screw-threaded bar 44 of the titration cylinder 46 is in engagement with an internally screw-threaded gear $43_a$ which meshes with the gear 43.

When the pulse motor 42 is energized, the two gears 43 and $43_a$ are rotated thereby elevating the screw-threaded bar 44. Thus, the piston 45 is elevated in proportion to the number of the pulses $P_1$ generated from the pulse generator 41, and a quantity $q_1$ of titrant proportional to the number of the pulses $P_1$ is dropped from the titrating cylinder 46 into the titrating vessel 2.

In the computer 33 the output pulses $P_1$ of a constant frequency delivered from the pulse generator 41 is counted and processed as described hereinbefore in connection with the previous embodiment shown in FIG. 4, and the titration result is indicated in a digital display device 39.

What is claimed is:

1. A titration controlling apparatus comprising an electrolytic cell including a pair of electrolytic electrodes and a detecting electrode; first analogue memory device for temporarily storing an electric signal obtained from the detecting electrode; a subtractor for subtracting said stored electric signal from an electric signal immediately following said electric signal; a division circuit receiving the output of the subtractor as a dividend; a second analogue memory device for temporarily storing the output of the division circuit; a third analogue memory device for temporarily storing the output of the second analogue memory device and for delivering an output to the division circuit as a divisor; and a voltage/current converter receiving the output of said second analogue memory device for supplying an electrolytic current to the electrolytic electrodes in the electrolytic cell.

2. A titration controlling apparatus as set forth in claim 1 which further comprises means responsive to the outputs of said second and third analogue memory devices for determining the end point of the titration.

3. A titration controlling apparatus comprising an electrolytic cell including a pair of electrolytic electrodes and a detecting electrode, data-processing means, a first voltage/frequency converting means for converting an output from said detecting electrode into a pulse train, a first signal coupling means for optically coupling an output of said first voltage/frequency converting means to an input of said data-processing means, electrolytic means for intermittently passing a controlled electrolytic current across said electrolytic electrodes, second signal coupling means for optically coupling an output of said data-processing means to an input of said electrolytic means, second voltage/frequency converting means for converting an electrolytic current signal from said electrolytic means into a pulse train, and a third signal coupling means for optically coupling an output of said second voltage/frequency converting means to another input of said data-processing means, said data-processing means further comprising a first operational member which receives the output from said detecting electrode through said first signal coupling means each time when an intermittent electrolysis is carried out in said electrolytic cell, to calculate and store a variation between two successive outputs from the detecting electrode, a second operational member wherein the quantity of electricity passed in the course of an immediately prior electrolysis is divided by said variation between the two successive outputs each time when an intermittent electrolysis is carried out in said electrolytic cell, whereby to preset the quantity of electricity for the immediately subsequent electrolysis, a third operational member which compares the preset quantity of electricity with an actual quantity of electricity passed through said electrolytic means to deliver an electrolysis controlling output when both of said quantities are equal thereby terminating the electrolytic current of each intermittent titration, a fourth operational member which terminates the entire titration upon finding an inflection point in a variation curve exhibiting variation caused by each intermittent titration, and a fifth operational member which integrates the quantity of electricity passed through the electrolytic cell and displays the integrated result.

4. A titration controlling apparatus as set forth in claim 3 wherein each of said photocoupler comprises a luminous diode and a phototransistor or a photodiode.

* * * * *